United States Patent [19]

Dirlikov

[11] Patent Number: 4,754,028

[45] Date of Patent: * Jun. 28, 1988

[54] 3,4,5-TRISELENA-TRICYCLO-[5.2.1.0.$^{2,6}$]DECANES AND DERIVATIVES THEREOF

[75] Inventor: Stoil K. Dirlikov, Midland, Mich.

[73] Assignee: The Dow Chemical Company, Midland, Mich.

[*] Notice: The portion of the term of this patent subsequent to Oct. 2, 2001 has been disclaimed.

[21] Appl. No.: 653,421

[22] Filed: Sep. 24, 1984

[51] Int. Cl.$^4$ ............................................ C07D 345/00
[52] U.S. Cl. ......................................... 540/1; 528/403
[58] Field of Search .......................... 260/239R; 540/1

[56] References Cited

U.S. PATENT DOCUMENTS

| | | | |
|---|---|---|---|
| 3,149,101 | 9/1964 | Hubel et al. | 260/239 R |
| 3,542,764 | 11/1970 | Mack | 260/239 R |
| 3,586,700 | 6/1971 | Kurtz et al. | 549/31 |
| 3,671,467 | 6/1972 | Gunther | 260/239 R |
| 3,723,417 | 3/1973 | Perez-Alberne | 260/239 R |
| 3,905,958 | 9/1975 | Gunther | 260/239 R |
| 3,971,742 | 7/1976 | Gunther | 260/239 R |
| 4,033,982 | 7/1977 | Hay | 549/31 |
| 4,097,474 | 6/1978 | Askew et al. | 549/31 |
| 4,233,131 | 11/1980 | Ratcliffe et al. | 260/239 R |
| 4,405,515 | 9/1983 | Engler et al. | 260/239 R |
| 4,474,970 | 10/1984 | Dirlikov | 549/31 |
| 4,505,858 | 3/1985 | Mayer | 260/239 R |
| 4,508,639 | 4/1985 | Camps et al. | 260/239 R |

FOREIGN PATENT DOCUMENTS 1490587 9/1974 United Kingdom .

OTHER PUBLICATIONS

*Journal Org. Chem.*, vol. 45, (1980), pp. 2632–2636.
Chemical Abstracts 82:125418s, 1975.
Lakshmikantham et al., *Tetrahedron Letters*, vol. 22, No. 42, pp. 4199–4200, 1981.

*Primary Examiner*—Donald G. Daus
*Assistant Examiner*—M. E. Krumnow
*Attorney, Agent, or Firm*—Paul D. Hayhurst

[57] ABSTRACT

Novel 3,4,5-Tri(selena- or tellura-)tricyclo[5.2.1.0.$^{2,6}$]-decanes and derivatives are prepared in high yield by contacting a bicyclo[2.2.1]hept-2-ene compound and selenium or tellurium in the presence of a solvent, and a catalyst.

15 Claims, No Drawings

3,4,5-TRISELENA-TRICYCLO-[5.2.1.0.$^{2,6}$]DECANES AND DERIVATIVES THEREOF

BACKGROUND OF THE INVENTION

This invention relates to a method for the production of certain novel cyclic compounds which contain selenium or tellurium or both.

The interaction of organic compounds with selenium or tellurium is known generally to result in somewhat unusual compounds which often are complex and polymeric. Typical preparative methods for said compounds require acetylenic compounds, diolefins, difunctional organic compounds, such as dihalides, or combinations of these. For example, U.S. Pat. No. 3,149,101 discloses the reaction between dihalobutadienes and a large class of compounds for form the corresponding heterocyclic dienes, e.g., tetraphenyltellurophene. The multi-step preparation of 1,2,3-triselenacyclopentane from 1,2-dibromoethane is disclosed in Volume 45 of the *J. Org. Chem.*, pp. 2632–6 (1980). The preparation of tellurium-containing heterocyclic compounds, such as cis-3,5-dibenzylidene-1,2,4-tritellurole from sodium phenylethynyltellurolate and ethereal HCl, is described in V. 22 (42) of *Tetrahedron Letters*, pp. 3199–200 (1981).

U.S. Pat. No. 3,671,467 discloses the reaction of difunctional organic molecules having functional moieties selected from the group consisting of "halides, epoxy and sulfonate ester groups and diazonium halides" with a difunctional reagent containing a diselenide. In particular, Example 1 of said patent discloses contacting sodium sulfite (Na$_2$So$_3$), selenium, water and 4,6-bis(-chloromethyl)-m-xylene at reflex temperature to prepare 4,6-bis(methyl)-m-xylene diselenide. Said patent further discloses that the products of the reaction generally described in this paragraph may be polymerized by reacting the products with additional elemental selenium, generally at temperatures of from about 200° C. to about 300° C. U.S. Pat. No. 3,971,742 describes a process which is similar to the process of U.S. Pat. No. 3,671,467 except that mixtures of selenium and tellurium are employed.

U.S. Pat. No. 4,233,131 discloses the production of compound such as ethylene episelenide by irradiating a mixture of elemental selenium and olefins of 2–6 carbon atoms with certain electromagnetic radiation. Thus, said process does not require the acetylenic compounds, etc., of the typical methods described hereinabove for the preparation of selenium- or tellurium-containing organic compounds. However, it does require the use of electromagnetic radiation.

Heretofore, novel 3,4,5-tri(selena- or tellura-)polycyclo compounds, as described hereinafter, and the corresponding polymers have not been prepared. It would be desirable to prepare said polycyclo compounds using a single process which would not require electromagnetic radiation or the acetylenic compounds, etc., of prior art processes.

SUMMARY OF THE INVENTION

The present invention includes novel monomeric 3,4,5-tri(selena- or tellura-)polycyclo monomers and their polymers. According to the method of the present invention, 3,4,5-tri(selena- or tellura-)polycyclo compounds, as hereinafter described, are produced by contacting selenium, tellurium, or both and a bicyclo[2.2.1-]hept-2-ene, or a derivative thereof, in the presence of a solvent and a catalyst under the proper reaction conditions. The method of the present invention is advantageous in that it obviates the need to use the acetylenic compounds, etc., of the prior art. The compounds of the present invention are useful in several applications, including uses as cross-linking agents, plasticizers, thermal stabilizer, antioxidants, monomers, polymers, and in certain photoconductive applications.

DETAILED DESCRIPTION OF THE INVENTION

The bicyclo[2.2.1]hept-2-ene compounds that are suitable for use in this invention are generally described by the formula

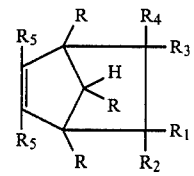

wherein each R, R$_1$, R$_2$, R$_3$, R$_4$ and R$_5$ is independently a moiety which does not prevent the reaction between the bicyclo[2.2.1]hept-2-ene and selenium and/or tellurium under the reaction conditions described herein. Examples of typical R, R$_1$, R$_2$, R$_3$ and R$_4$ moieties include hydrogen, halogen, alkyl of from 1 to about 15 carbon atoms, aryl of from about 6 to about 15 carbon atoms, or cycloalkyl of from about 4 to about 10 carbon atoms; R$_1$ and R$_3$ may further be independently chosen from alkenyl of from 2 to about 10 carbon atoms, hydroxyl, hydroxyalkyl having from 1 to about 10 carbon atoms, dialkylamino having from 1 to about 10 carbon atoms, dialkylaminoaklyl wherein the alkyl groups have from 1 to about 4 carbon atoms, and alkoxy having from 1 to about 10 carbon atoms; R$_1$ and R$_2$ when taken together and R$_3$ and R$_4$ when taken together can be alkylidene of from 1 to about 6 carbon atoms; R$_1$ and R$_3$ when taken together can be —CHYCH═CY— wherein Y is hydrogen or methyl. Typically, each R$_5$ independently is hydrogen or alkyl of from 1 to about 15 carbon atoms. These compounds are also described in U.S. Pat. Nos. 3,586,700 and 4,033,982, the teachings of which, with respect to these compounds, are incorporated herein by reference. Preferred bicyclo[2.2.1-]hept-2-ene compounds include, for example, dicyclopentadiene, bicyclo[2.2.1]hept-2-ene and 5-ethenyl-bicyclo[2.2.1]hept-2-ene.

The source of selenium can be elemental selenium, which is preferred, or polyselenides. Similarly, elemental tellurium and polytellurides can be employed.

Theoretically, 3 moles of selenium or tellurium atoms are necessary per mole of bicyclo[2.2.1]hept-2-ene compound in order to produce the corresponding triselane or tritellurane. Preferably, from about 2.8 to about 3 g-atoms of selenium or tellurium are employed per g-mole of bicyclo[2.2.1]hept-2-ene compound. Larger or smaller amounts of selenium or tellurium can be used, if desired, however, pentacyclic compound formation may be observed at selenium or tellurium/bicyclo[2.2.1-]hept-2-ene compound ratios greater than 3.

Selenide, telluride or sulfide ions catalyze the reaction of the present invention. Examples of suitable catalysts include alkali metal sulfides, alkaline earth metal sulfides, alkaline earth metal mercaptides and alkali metal mercaptides, and the corresponding selenides and tellurides. Preferred catalysts include anhydrous sodium sulfide, sodium sulfide nonahydrate (Na$_2$S.9H$_2$O) and sodium phenylthiolate. In the practice of the present invention, it is preferred that the catalyst be in solution. Any amount of selenide, telluride or sulfide ions may be used as long as the reaction is catalyzed by those ions. Typically, from about $1 \times 10^{-10}$ to about 1 mole of selenide, telluride or sulfide ions are employed per mole of bicyclo[2.2.1]kept-2-ene compound employed; preferably from about $1 \times 10^{-5}$ to about 0.01 mole of selenide, telluride or sulfide ions are employed per mole of bicyclo[2.2.1]hept-2-ene compound. Most preferably, the amount of selenide, telluride or sulfide ions will range from about 0.001 to about 0.01 mole of selenide, telluride or sulfide ions per mole of bicyclo[2.2.1]hept-2-ene compound.

Selenide, telluride or sulfide ions are advantageously employed in the form of a soluble selenide, telluride or sulfide compound. For the purposes of the present invention, the term soluble selenide, telluride or sulfide compound refers to selenide telluride or sulfide ion-containing compounds which are soluble in one of the possible solvent systems which are suitable for use in the method of the present invention. Thus, almost any selenide, telluride or sulfide ion-containing compound is a soluble selenide, telluride or sulfide compound because there are many solvent systems which are capable of solvating the various components of the reaction mixture, i.e., catalyst and reactants, to form a homogeneous mixture. For example, sodium sulfide is soluble in many polar solvents, but is insoluble in most non-polar solvents at the typically employed reaction temperatures.

Ammonia and certain organic amines, such as aniline, can be employed as the catalyst. The ammonia catalyst can be introduced into the reaction mixture either before the reaction has been started or during the reaction; the manner of addition is not critical. A preferred procedure is to bubble the ammonia in the form of a gas through a mixture of the reactants; one can also bubble the ammonia through a mixture of less than all of the reactants and then add the remaining reactants. The concentration thereof is not critical and can be varied widely; the sole requirement is that a catalytically effective amount be present sufficient to permit the production of the 3,4,5-tri(selena- or tellura-)polycyclo compounds.

A wide number of solvents and combinations of solvents may be employed in the practice of the present invention. Polar organic solvents and combinations of polar and other inert organic co-solvents are preferred. Typical polar organic solvents and combinations of solvents are described in U.S. Pat. No. 3,586,700, the teachings of which, with respect to solvents, are incorporated herein by reference. An example of a preferred combination of solvents is dimethylformamide in combination with pyridine. Non-polar or inert organic solvents may be used alone provided that, if the catalyst employed is not soluble in said solvent, a phase-transfer agent is employed therewith for the purpose of aiding the dissolution of the catalyst. Any phase-transfer agent which aids the dissolution of the catalyst into the reaction solution may be employed. Several suitable phase-transfer agents are well-known, including for example, dibenzo-18-crown-6 ether and bis(triphenylphosphine)iminium chloride. Typical non-polar solvents include aliphatic and aromatic hydrocarbons such as heptane, cyclohexane, 3-methylpentane, isooctane, cumene, toluene and the like. toluene is an example of a preferred non-polar solvent.

Any amount of solvent may be employed as long as it is sufficient to dissolve the final product. Typically, from about 100 to about 2000 ml of solvent are employed per mole of bicyclo[2.2.1]hept-2-ene compound. Preferably, from about 800 to about 1200 ml of solvent are employed per mole of bicyclo[2.2.1]hept-2-ene compound.

In general, any reaction temperature can be employed wherein the thermal reaction kinetics are not deleterious to reaction rates, reaction time, yield and/or conversion of the bicyclo[2.2.1]hept-2-ene compounds to the desired 3,4,5-tri(selena- or tellura-)polycyclo compounds. Typically, the reaction temperatures can be varied widely, however, they often fall within the range of from about 50° C. to about 150° C. and preferably the reaction is conducted within the temperature range of from about 90° C. to about 120° C. The reaction is typically performed at atmospheric pressure, although sub- or superatmospheric pressures may be employed if desired.

Any reaction period can be employed, however, generally effective reaction periods fall within the range of from about 1 hour to about 50 hours. The process is preferentially carried out in the presence of an inert atmosphere of nitrogen in order to exclude from the reaction medium any oxygen or oxidizing agents which are well-known to oxidize organic sulfides to sulfoxides or sulfones or other undesirable reaction products.

When the reactants, catalyst and solvent(s) are properly combined under reaction conditions as hereinbefore specified, a 3,4,5-tri(selena- or tellura-)polycyclo product will be formed. The novel 3,4,5-tri(selena- and or tellura-)polycyclo product compounds of the present invention are generally described by the formula:

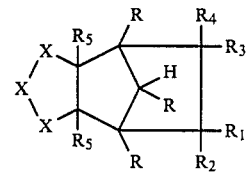

wherein X independently is selenium or tellurium and the other substituents are as previously described.

The crude product of the reaction may be treated by known methods, such as those described in Example 1, to recover the desired products.

The product compounds exist in equilibrium between the monomeric and polymeric forms. The general formula for the monomeric form is given immediately hereinabove. The polymeric form has a repeating unit of the general formula

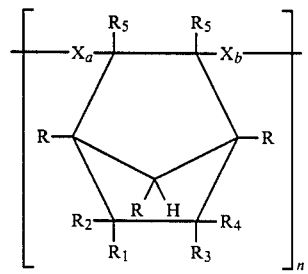

wherein R, $R_1$, $R_2$, $R_3$, $R_4$, $R_5$ and X are as defined hereinabove, wherein n is at least about 2, and wherein the quantity $((a+b)/2)$ has a value of 3. As a general rule, the equilibrium shifts to the monomeric form when the product is in solution, and shifts to the polymeric form in the absence of solvent. Polymerization can be done using the techniques of U.S. Pat. No. 3,586,700, the teachings of which are incorporated herein by reference with respect to polymerization techniques.

The following example is given to illustrate the invention and should not be construed as limiting its scope.

EXAMPLE 1

Three-tenths of a g-atom of gray selenium (23.67 g), 1 mole of norbornylene (94.16 g), 0.0021 mole of anhydrous sodium sulfide (0.156 g), 1400 ml of pyridine and 70 ml of dimethylformamide are added to a 2-liter, three-necked, glass flask which is equipped with means for admitting gas thereto, a stirring means, and a condensing means. Nitrogen gas is admitted to the flask to purge the flask of atmospheric air. The contents of the flask are heated up to 110° C. and that temperature is maintained for 15 hours. The flask is allowed to cool to about 25° C. and unreacted selenium is filtered from the reaction mixture. The solvent is then evaporated at 45° C. under a vacuum in a rotary vacuum evaporator to obtain a solid product. The solid is washed with methanol to separate the pure product from the impurities. The product is dried under vacuum at about 25° C. to give 34.86 g of exo-3,4,5-triselenatricyclo[2.2.1]hept-2-ene. The selenium content of the solid product is 71.39 weight percent. The solid product is a yellow powder and has a slight garlic-like odor.

The monomeric product which forms in Example 1 is analyzed using 60 MHz nuclear magnetic resonance.

What is claimed is:

1. A 3,4,5-triselenapolycyclo compound of the formula:

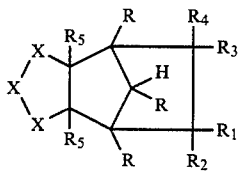

wherein X is selenium and wherein each R, $R_1$, $R_2$, $R_3$, $R_4$ and $R_5$ is independently hydrogen, halogen, alkyl of from 1 to about 15 carbon atoms, aryl of from about 6 to about 15 carbon atoms, or cycloalkyl of from about 4 to about 10 carbon atoms; $R_1$ and $R_3$ further can be independently chosen from alkenyl of from 2 to about 10 carbon atoms, hydroxyl, hydroxyalkyl having from 1 to about 10 carbon atoms, dialkylamino having from 1 to about 10 carbon atoms, dialkylaminoalkyl wherein the alkyl groups have from 1 to about 4 carbon atoms, and alkoxy having from 1 to about 10 carbon atoms; each $R_5$ is independently hydrogen or alkyl of from 1 to about 15 carbon atoms; $R_1$ and $R_2$ when taken together and $R_3$ and $R_4$ when taken together are alkylidene of from 1 to about 6 carbon atoms; $R_1$ and $R_3$ when taken together are —CHYCH=CY— wherein Y is hydrogen or methyl.

2. A compound of claim 1 wherein R, $R_1$, $R_2$, $R_3$, $R_4$, and $R_5$ are hydrogen.

3. A compound of claim 1 wherein $R_1$ and $R_3$ when taken together are —CHYCH=CY—.

4. A process comprising contacting a catalyst comprising selenide or sulfide ions, a bicyclo[2.2.1]hept-2-ene and selenium under reaction conditions sufficient to form a compound of claim 1.

5. The process of claim 4 wherein the catalyst is sodium sulfide.

6. The process of claim 4 wherein a solvent comprising a polar solvent is employed.

7. The process of claim 6 wherein the polar solvent comprises a mixture of pyridine and dimethylformamide.

8. The process of claim 4 conducted in the substantial absence of phenols.

9. The process of claim 4 wherein a solvent comprising a non-polar solvent is employed.

10. The process of claim 9 wherein a phase-transfer agent is employed.

11. The process of claim 9 wherein the solvent is toluene.

12. A process wherein selenium is contacted with a bicyclo[2.2.1]hept-2-ene in the presence of a sodium sulfide catalyst under such conditions that a 3,4,5-triselenapolycyclo compound is formed.

13. The process of claim 12 wherein the 3,4,5-triselenapolycyclo compound is 3,4,5-triselenatetracyclo[5.5.1.0.$^{2,60.8,12}$]tridec-9-ene, 8-ethenyl-3,4,5-triselenatricyclo[5.2.1.0.$^{2,6}$]decane, or 3,4,5-triselenatricyclo[5.2.1.0.$^{2,6}$]decane.

14. The process of claim 13 wherein the contacting is performed in the presence of dimethylformamide and pyridine.

15. The process of claim 14 wherein the catalyst is anhydrous sodium sulfide.

* * * * *

UNITED STATES PATENT AND TRADEMARK OFFICE
CERTIFICATE OF CORRECTION

PATENT NO. : 4,754,028
DATED : June 28, 1988
INVENTOR(S) : Stoil K. Dirlikov

It is certified that error appears in the above-identified patent and that said Letters Patent is hereby corrected as shown below:

Col. 1, line 17, "for" should read -- to --;

lines 23-24, "phenylethnyltellurolate" should read -- phenylethynyltellurolate --;

line 25, "3199-200" should read -- 4199-200 --;

line 33, "reflex" should read -- reflux --;

line 44, "compound" should read -- compounds --.

Col. 2, line 6, "stabilizer" should read -- stabilizers --;

line 36, "dialkylaminoaklyl" should read -- dialkylaminoalkyl --.

Col. 3, line 9, "bicyclo[2.2.1]kept-2-ene" should read -- bicyclo[2.2.1]hept-2-ene --.

Col. 4, line 1, second occurrence of "toluene" should read -- Toluene --;

lines 34-35, "and or" should read -- and/or --.

Signed and Sealed this

Twenty-sixth Day of September, 1989

Attest:

DONALD J. QUIGG

Attesting Officer

Commissioner of Patents and Trademarks